(12) United States Patent
Springer et al.

(10) Patent No.: US 10,350,061 B2
(45) Date of Patent: Jul. 16, 2019

(54) INTRAOCULAR LENS INSERTION DEVICE

(71) Applicant: ABBOTT MEDICAL OPTICS INC., Santa Ana, CA (US)

(72) Inventors: Kevin R. Springer, Santa Ana, CA (US); David A. Ruddocks, Mission Viejo, CA (US); Mark S. Cole, Trabuco Canyon, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 179 days.

(21) Appl. No.: 15/349,925

(22) Filed: Nov. 11, 2016

(65) Prior Publication Data

US 2017/0135811 A1    May 18, 2017

Related U.S. Application Data

(60) Provisional application No. 62/255,283, filed on Nov. 13, 2015.

(51) Int. Cl.
*A61F 2/16* (2006.01)
(52) U.S. Cl.
CPC ............ *A61F 2/1678* (2013.01); *A61F 2/167* (2013.01); *A61F 2/1662* (2013.01);
(Continued)
(58) Field of Classification Search
CPC ...... A61F 2/167; A61F 2/1662; A61F 2/1675; A61F 2/1678; A61F 2/1672
See application file for complete search history.

(56) References Cited

U.S. PATENT DOCUMENTS 3,674,181 A * 7/1972 Marks ................... A61F 11/00
222/179.5
6,086,559 A 7/2000 Enk
(Continued)

FOREIGN PATENT DOCUMENTS

AU 2012211307 B2 8/2015
CN 104136054 A 11/2014
(Continued)

OTHER PUBLICATIONS

International Search Report and Written Opinion for Application No. PCT/US2016/061687, dated Jan. 31, 2017, 15 pages.

*Primary Examiner* — Thomas M McEvoy
(74) *Attorney, Agent, or Firm* — Johnson & Johnson Surgical Vision, Inc.

(57) ABSTRACT

Accordingly, embodiments of the present invention provide an IOL insertion device that facilitates the injection of the IOL in a controlled manner. The insertion device includes a front modular portion and an injector. The modular portion may be preloaded with an IOL and coupled with the injector. The injector includes a distal portion, a body, and a plunger. The distal portion includes a front seal which has a longitudinal bore at the center, through which a distal portion of the plunger passes. The plunger tip is tapered. The plunger also includes a sealing element situated between its distal portion and its proximal portion. The sealing element includes a small aperture through which a fluid, such as a viscoelastic or a balanced salt solution ("BSS") and the like, may pass toward the proximal end of the body when the plunger advances distally. As the fluid passes through the small aperture on the sealing element on the plunger, a constant speed and force is maintained as the IOL is ejected into the eye.

19 Claims, 7 Drawing Sheets

(52) U.S. Cl.
CPC .......... *A61F 2/1664* (2013.01); *A61F 2/1672* (2013.01); *A61F 2/1675* (2013.01)

(56) References Cited

U.S. PATENT DOCUMENTS

| | | |
|---|---|---|
| 7,901,377 B1 | 3/2011 | Harrison et al. |
| 9,119,920 B2 | 9/2015 | Cowe |
| 2006/0235429 A1 | 10/2006 | Lee et al. |
| 2010/0185205 A1* | 7/2010 | Novakovic ........... A61F 2/1662 606/107 |
| 2010/0191347 A1 | 7/2010 | Pusch et al. |
| 2014/0031832 A1 | 1/2014 | Catlin et al. |
| 2015/0066043 A1 | 3/2015 | Nallakrishnan |
| 2016/0074156 A1* | 3/2016 | Raquin ................. A61F 2/1678 606/107 |

FOREIGN PATENT DOCUMENTS

| | | |
|---|---|---|
| EP | 0937443 B1 | 5/2004 |
| EP | 2218473 B1 | 8/2011 |
| EP | 2716316 A1 | 4/2014 |
| EP | 1755713 B1 | 7/2014 |
| EP | 2913029 A1 | 9/2015 |
| GB | 2397767 A | 8/2004 |
| GB | 2397767 B | 7/2006 |
| KR | 101401270 B1 | 5/2014 |
| WO | 8810129 A1 | 12/1988 |
| WO | 2011032731 A1 | 3/2011 |
| WO | WO2012027517 * | 3/2012 |
| WO | 2013159045 A1 | 10/2013 |
| WO | 2014053495 A1 | 4/2014 |
| WO | 2014089250 A1 | 6/2014 |
| WO | 2014164685 A1 | 10/2014 |
| WO | WO2014187612 * | 11/2014 |
| WO | 2015073740 A2 | 5/2015 |

* cited by examiner

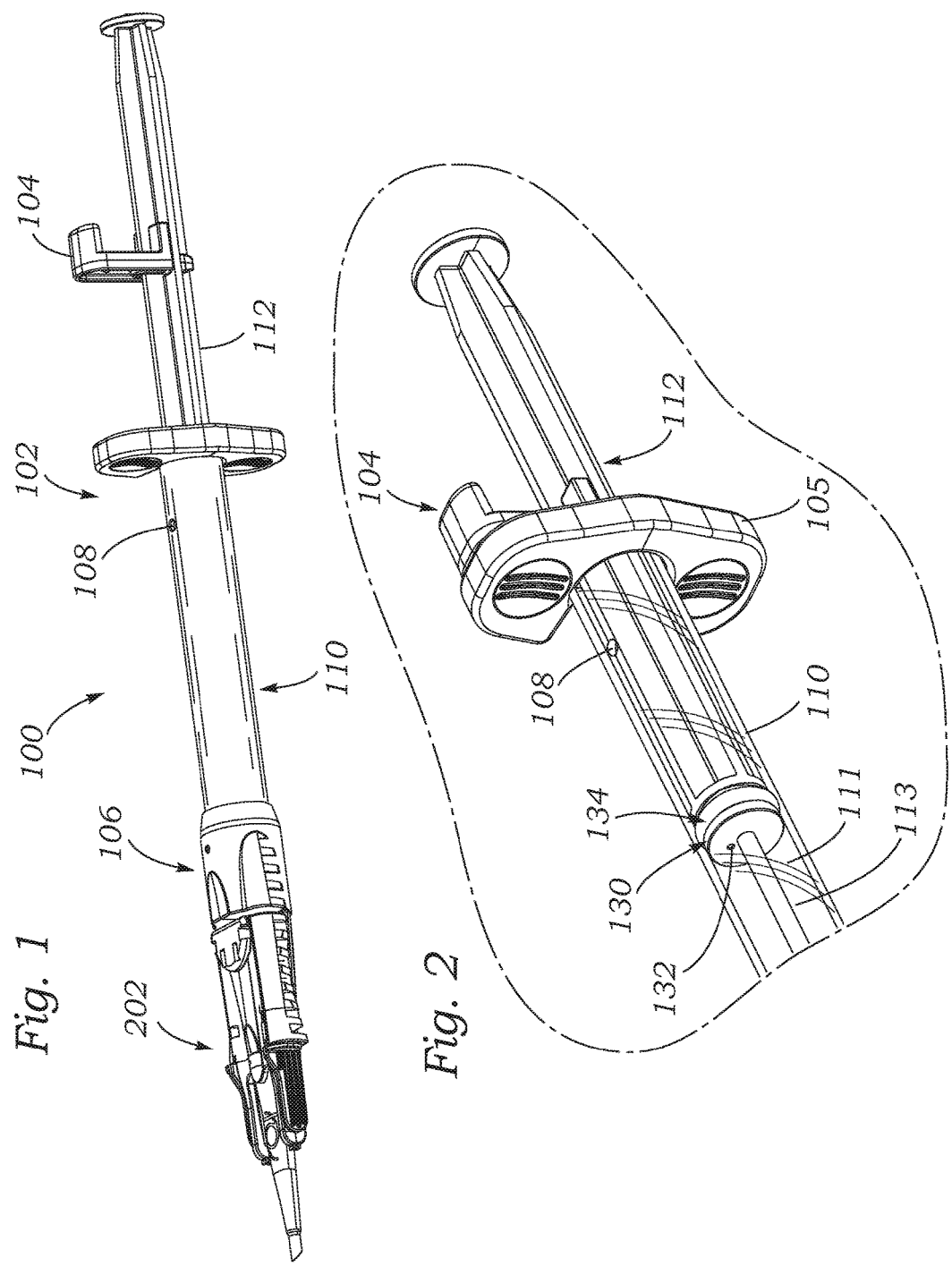

INTRAOCULAR LENS INSERTION DEVICE

CROSS-REFERENCE TO RELATED APPLICATIONS

This application claims the benefit under 35 U.S.C. § 119(e) of U.S. Provisional Patent Application No. 62/255,283, filed Nov. 13, 2015, the full disclosures of which are incorporated herein by reference.

This application also incorporates by reference in its entirety U.S. Pat. No. 7,892,282 filed on Apr. 8, 2005.

TECHNICAL FIELD

Embodiments of the present invention generally relate to an insertion device used in the surgical field for inserting intraocular lens ("IOL") into the eye, and more specifically to an insertion device that utilizes a plunger for controllably inserting an IOL into an eye by dampening the acceleration as the IOL is ejected.

BACKGROUND

IOLs are commonly implanted in the eye to treat certain conditions, such as cataracts or myopia. For example, an IOL is implanted in the eye as a replacement for the natural crystalline lens after cataract surgery or to alter the optical properties of an eye, such as by providing vision correction, in which the natural lens remains. The IOL provides the light focusing function originally undertaken by the crystalline lens. Insertion of an IOL for the treatment of cataracts is the most commonly performed eye surgical procedure. Each year approximately 1.4 million people in the United States alone undergo cataract surgery.

A typical IOL includes an optic or lens body for focusing light toward the retina of the eye. In addition, the IOL also includes one or more fixation members or haptics for securing the IOL in the desired position within the chamber of the eye. The IOL is implanted directly into the eye through a small incision formed in the ocular tissue of the eye. To fit through this small incision, modern IOLs, which are made from soft, biocompatible materials, are designed to be deformed, e.g., rolled, folded or the like, to a relatively small profile before being injected into the eye and then allowed to return to their original shape within the eye.

Generally, IOL insertion devices use a plunger to insert the IOL into the eye. It is advantageous to have a small incision in the eye to insert an IOL. Accordingly, a small diameter tube that tapers is typically used. As the IOL progresses down the tapering tube, increased force is needed. Then, as the IOL is being expelled, the resistant force dramatically decreases. Consequently, the expelled IOL has a tendency to pop open into place within the eye. Thus, in existing plunger-type IOL insertion devices, there is an increased risk of damaging the eye if the IOL rapidly expels out of the insertion device. This phenomenon of an IOL rapidly ejecting due to a decrease in resistant force is commonly referred to as popping.

Therefore, it would be highly beneficial to provide an IOL insertion device that facilitates the injection of the IOL in a controlled manner by dampening the acceleration that occurs as the IOL is pushed out of the insertion device. Furthermore, it would be beneficial for the insertion device to provide an adaptive or accommodative force that changes depending upon the amount of force imparted on the plunger by the user.

SUMMARY

Accordingly, embodiments of the present invention provide an IOL insertion device that facilitates the injection of the IOL in a controlled manner. The insertion device includes a front modular portion or cartridge and an injector. The modular portion or cartridge may be loaded with an IOL (either manually or preloaded) and coupled with the injector. The injector includes a distal portion, a body, and a plunger. The distal portion includes a front seal which has a longitudinal, bore at the center, through which a distal portion of the plunger passes. The bore may be asymmetrical. The plunger tip is tapered. The plunger also includes a sealing element situated between its distal portion and its proximal portion. The sealing element includes a small aperture through which a fluid, such as a viscoelastic or a balanced salt solution ("BSS") and the like, may pass toward the proximal end of the body when the plunger advances distally. As the fluid passes through the small aperture on the sealing element on the plunger, a constant speed and force is maintained as the IOL is ejected into the eye.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

Understanding this invention will be facilitated by the following detailed description of the preferred embodiments considered in conjunction with the accompanying drawings, in which like numerals refer to like parts. Note, however, that the drawings are not drawn to scale.

FIG. 1 illustrates a perspective view of an IOL insertion device according to an embodiment of this invention.

FIG. 2 illustrates a view of the proximal end of an IOL insertion device according to an embodiment of this invention.

DETAILED DESCRIPTION

Figure 3:
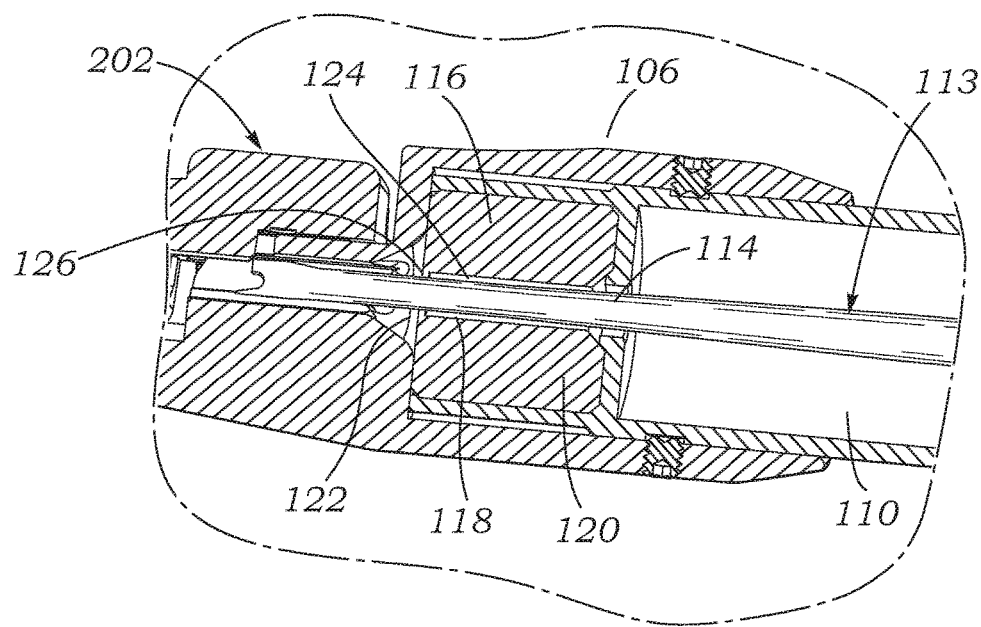
FIG. 3 illustrates a sectional view of a distal portion of an injector of an IOL insertion device according to an embodiment of this invention.

The present invention is directed to a system including methods and devices of implantation of deformable IOL structures for surgical placement in the eye.

The drawings and related descriptions of the embodiments have been simplified to illustrate elements that are relevant for a clear understanding of these embodiments, while eliminating various other elements found in conventional IOL insertion devices. Those of ordinary skill in the art may thus recognize that other elements and/or steps are desirable and/or required in implementing the embodiments that are claimed and described. But, because those other elements and steps are well known in the art, and because they do not necessarily facilitate a better understanding of the embodiments, they are not discussed. This disclosure is directed to all applicable variations, modifications, changes, and implementations known to those skilled in the art. As such, the following detailed descriptions are merely illustrative and exemplary in nature and are not intended to limit the embodiments of the subject matter or the uses of such embodiments. As used in this application, the terms "exemplary" and "illustrative" mean "serving as an example, instance, or illustration." Any implementation described as exemplary or illustrative is not meant to be construed as preferred or advantageous over other implementations. Further, there is no intention to be bound by any expressed or implied theory presented in the preceding background of the invention, summary, or the following detailed description.

In the following description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As explained above, some medical conditions, such as cataract and myopia, require the surgical replacement or augmentation of the eye's natural lens. Such procedures involve the insertion of an IOL into the eye through a small incision. To perform such procedures while minimizing the trauma caused to the treated eye, incisions between 1-4 mm (preferably less than 2 mm) may be employed. Such incisions are typically significantly smaller than the IOL itself. Therefore, to insert the IOL into the eye, modern IOLs, which are made from soft, biocompatible materials and are designed to be deformed, e.g., rolled, folded or the like, are deformed during the insertion process and are stored in the insertion device. The IOLs retain their deformed shape due to the resistant force inside the insertion device. The insertion device's tip, which is designed to be smaller than the incision in the eye, is used to feed the IOL into the eye. After insertion, the IOL may then naturally expand within the eye and may be position as needed by the surgeon.

However, many existing IOL insertion devices are not designed to insert the IOL into the eye in a controlled manner. The phenomenon of an IOL rapidly ejecting into the eye due to a decrease in resistant force is commonly referred to as popping.

Accordingly, to deform the IOL and insert it in a controlled manner through a small incision, example embodiments of the present invention may provide an insertion device. Such an insertion device may allow an IOL to be loaded in a chamber and may provide a mechanism which forces the IOL into the eye through an opening of an appropriate size. For example, some such devices may employ a tapering tube or cartridge, through which the IOL is inserted. Using such a device, the IOL may first be loaded into a chamber or opening in the insertion device. Loading may be a relatively simple process, as the chamber or opening may be large enough to easily hold the IOL without significantly compressing or deforming the IOL. The IOL may then be moved through a tapering tube. As the IOL travels through the tube, the diameter of the tube may decrease, compressing the IOL until it is deformed into a shape small enough for insertion.

Referring now to the drawings, wherein like reference numerals designate identical or corresponding parts throughout the several views and embodiments, an insertion device 100 in accordance with the present invention is illustrated in FIGS. 1 to 9.

Figure 7:
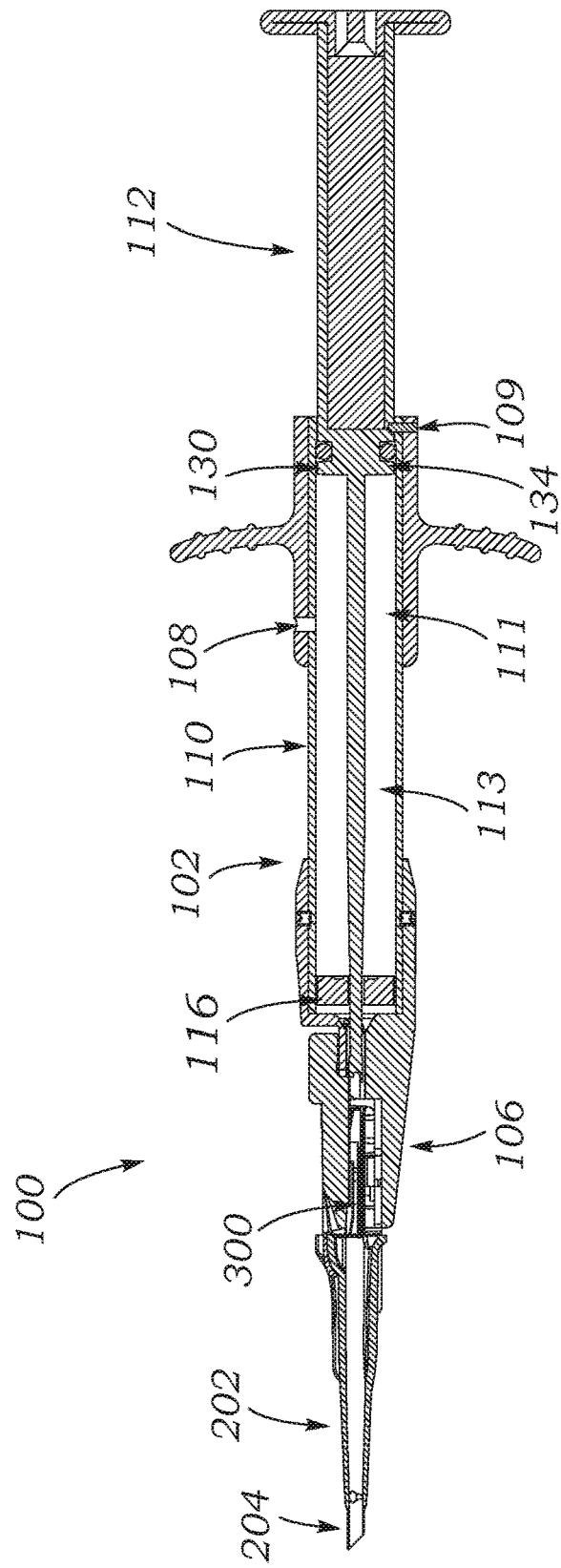
FIG. 7 illustrates a perspective view of an IOL insertion device according to an embodiment of this invention.

FIG. 1 shows an exemplary embodiment of a perspective view of the insertion device 100. The insertion device 100 includes a cartridge or front modular portion 202, and an injector 102. The injector 102 generally includes a body 110, a distal portion 106, and a plunger 112. While FIG. 1 shows a tubular body 110, the body 110 may also be an irregular curved shape, a polygon or in the shape of a D to control the pushrod orientation. The body 110 includes an aperture 108. The plunger 112 may be of any shape that facilities its movement within the tubular body 110. For example, the plunger 112 may have a hollow enclosed structure as shown in FIG. 7 or a multi-bladed open casing as shown in FIG. 1. The plunger 112 includes a stop 104. It is also envisioned that the plunger 112 may house an O-ring 134. The O-ring 134 may be a part of the plunger 112 or maybe an individual component that can be attached to the plunger 112. The O-ring 134 may have an outer diameter that produces a sliding fit with the inner diameter of the body 110. In an embodiment, there may be a vent 109 at a distal end of the body 110 that facilitates the ejectment of the fluid from the casing of the plunger 112 or from the rear end of the chamber 111.

During the insertion of the IOL, a fluid such as water or a viscoelastic substance or a BSS and the like may be used to facilitate the passing of the IOL through the insertion device 100. The fluid may be inserted into an opening in the cartridge and/or the chamber of the body 110 through the aperture 108. Alternatively, the fluid may be preloaded into the body 110. In an embodiment, the insertion device 100 may also include a plug. The plug may be used to close the aperture 108 such that the end user may remove the plug to fill the body 110 with the fluid and then close the aperture 108 using the plug after filling the body 110 with the fluid.

In an embodiment, the plug may be used to close the vent 109 at the distal end of the body 110. In an embodiment, two separate plugs may be used to close both the aperture 108 and the vent 109 at the distal end of the plunger 112. The plug may be a separate element or attached to the insertion device 100. In an embodiment, the plug or plugs may be inserted during the manufacture process after preloading the fluid into the body 110 to avoid spillage during packing and storage.

Figure 9:
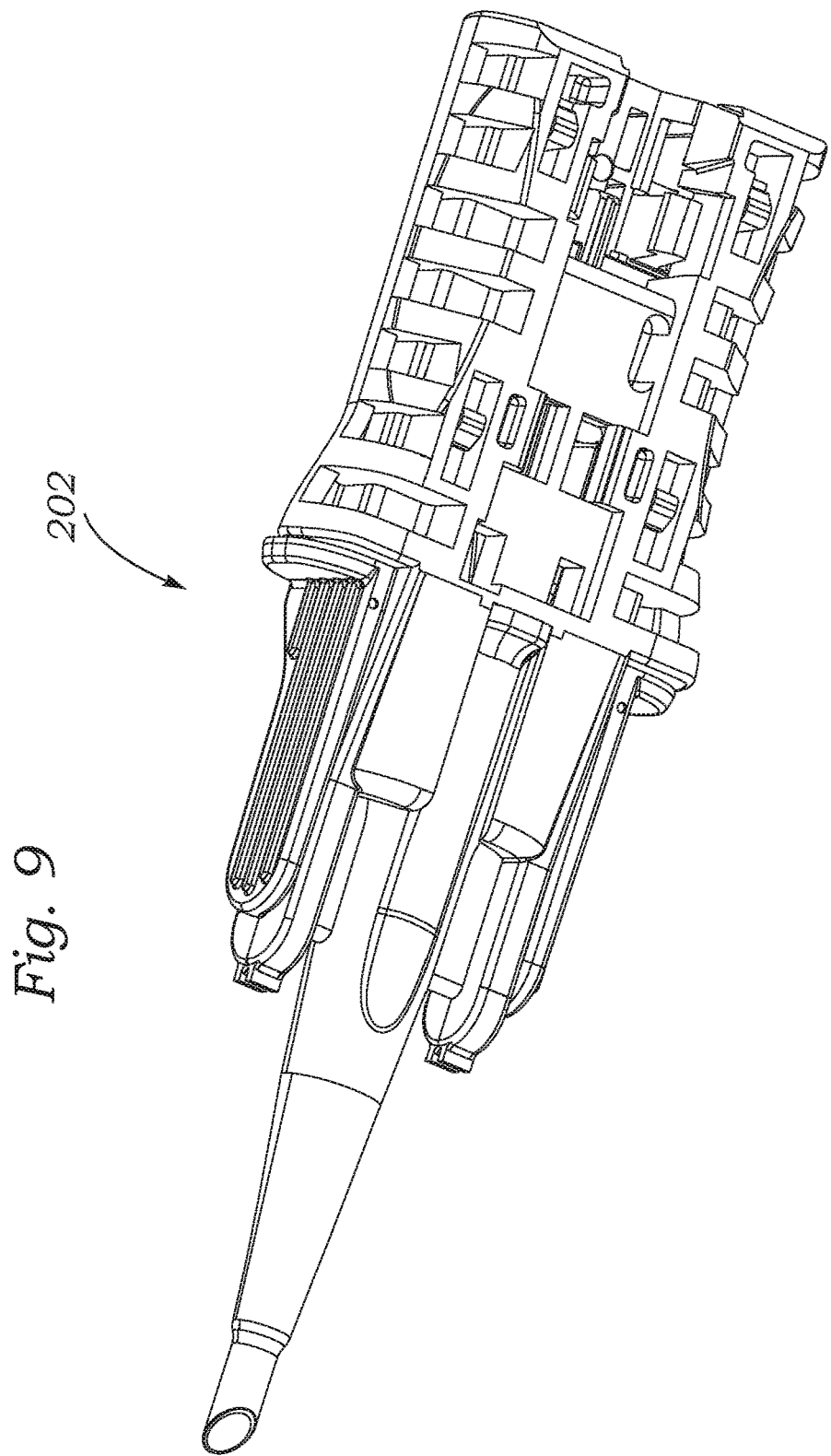
FIG. 9 illustrates a perspective view of the bottom of a modular portion of an IOL insertion device according to an embodiment of this invention.

Referring to FIG. 2, in an exemplary embodiment, a perspective view of the proximal end of the insertion device 100 is shown, with a partial sectional view of the body 110. As shown in FIG. 1 and described above, the insertion device 100 includes a body 110, a flange 105, a plunger 112, and a stop 104. The body 110 includes an aperture 108. The plunger 112 includes an elongated distal portion 113. A sealing element 130 is fixedly connected between, and separates, the elongated distal portion 113 and the proximal end of the plunger 112. The plunger 112 slides along the longitudinal length of the body 110. When the plunger 112 is pressed into the distally-advanced locked position, as shown in FIG. 2, the stop 104 rests against the flange 105 to stop the plunger 112 from advancing further. The plunger 112 may also house an O-ring 134 that slides across inner surface of the body 110 as the plunger 112 is advanced distally. The O-ring 134 may be attached to the sealing element 130 or to any other portion of the plunger 112. In this distally-advanced locked position, the IOL (not shown in the Figure) is loaded into the cartridge or front modular portion 202, and ready to be inserted into the eye, as seen in FIG. 9 and detailed below. In some embodiments, in the distally-advanced position, the O-ring 134 seals the aperture 108. As mentioned above, in some embodiments, fluid is initially inserted into the chamber 111 of the body 110 through the aperture 108. While fluid is being inserted into the chamber 111, the plunger 112 is in a proximally retracted position (not shown in the picture) so that the element 130 is proximally behind (toward the rear of) the aperture 108. While the fluid is being inserted into the chamber 111 through the aperture 108, the O-ring 134 is proximally behind the aperture 108, as well.

Figure 4:
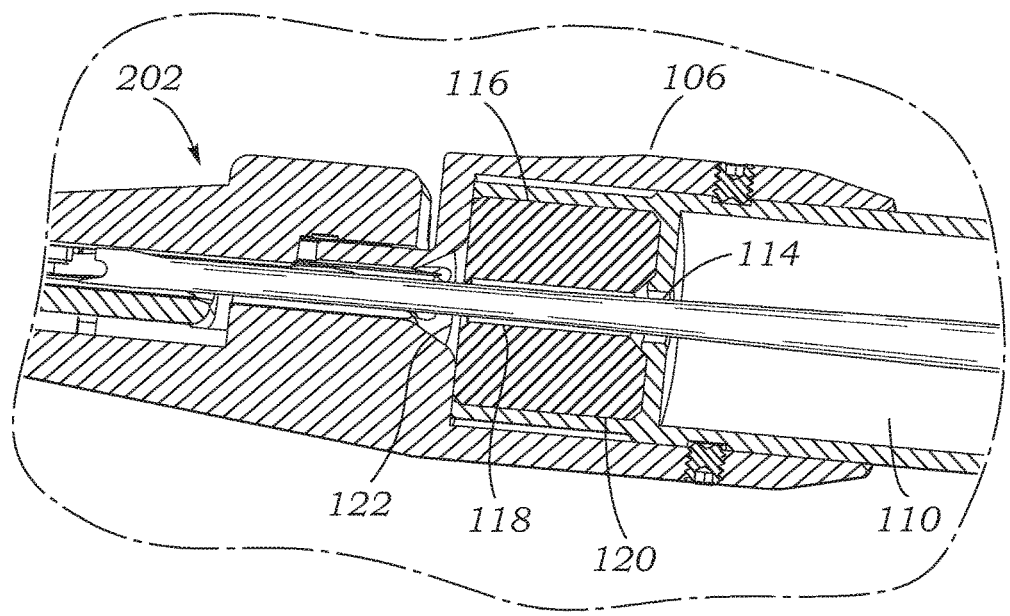
FIG. 4 illustrates another sectional view of a distal portion of an injector of an IOL insertion device according to an embodiment of this invention.

Referring to FIGS. 3 and 4, in an exemplary embodiment, a sectional view of the distal portion 106 of the injector 102 is shown. The distal portion 106 includes a front seal 116. The distal portion 106 includes the front seal 116. The front seal 116 has an asymmetrical bore 118, which extends longitudinally from the proximal end 120 to the distal end 122. At the distal end of the longitudinal, asymmetrical bore 118, there is a flap 126 that initially prevents fluid from passing until the plunger 112 is initially depressed. The distal portion 113 of the plunger 112 includes an elongated tip portion 114. The elongated tip portion 114 is adapted to pass through the longitudinal, asymmetrical bore 118. The elongated tip portion 114 is tapered and is smaller toward the distal end. As shown in FIG. 3, when the plunger 112 has not yet been pressed, there is a gap 124 between the outer surface of the elongated tip portion 114 and the surface of the longitudinal, asymmetrical bore 118. This gap 124 allows fluid to enter the cartridge 202 as the plunger 112 is depressed. The flap 126 at the distal end of the bore 118 initially retains the fluid in the gap, but as the plunger 112 is depressed, the elongated tip portion 114 breaks open the flap 126, and the fluid flows into the cartridge 202. It is also envisioned that the elongated tip portion 114 may have grooves that facilitate flowing of fluid into the cartridge or front modular portion 202 as the plunger 112 is depressed. The entry of the fluid into the cartridge of front modular portion 202 may serve a hydration or lubrication purpose.

The bore 118 herein has been described as asymmetrical. In an alternate embodiment, not shown, the bore 118 may be symmetrical. In this configuration, the plunger 112 may be guided by structures outside of the bore. By way of example, and not of limitation, such structures may include a protrusion on the plunger 112 which fits within a groove in the body 110. Conversely, there may be a protrusion on the body 110 which fits within a groove on the plunger 112.

When the plunger 112 is depressed and the elongated tip portion 114 advances to the distally-advanced locked position the wider portion of the elongated tip portion 114 fully engages the asymmetrical bore 118, as shown in FIG. 4. As will be described herein, in this engaged position, no fluid (e.g., BSS) will pass through the bore 118 from the inner chamber 111 of the body 110 into the cartridge or modular portion 202.

Figure 5:
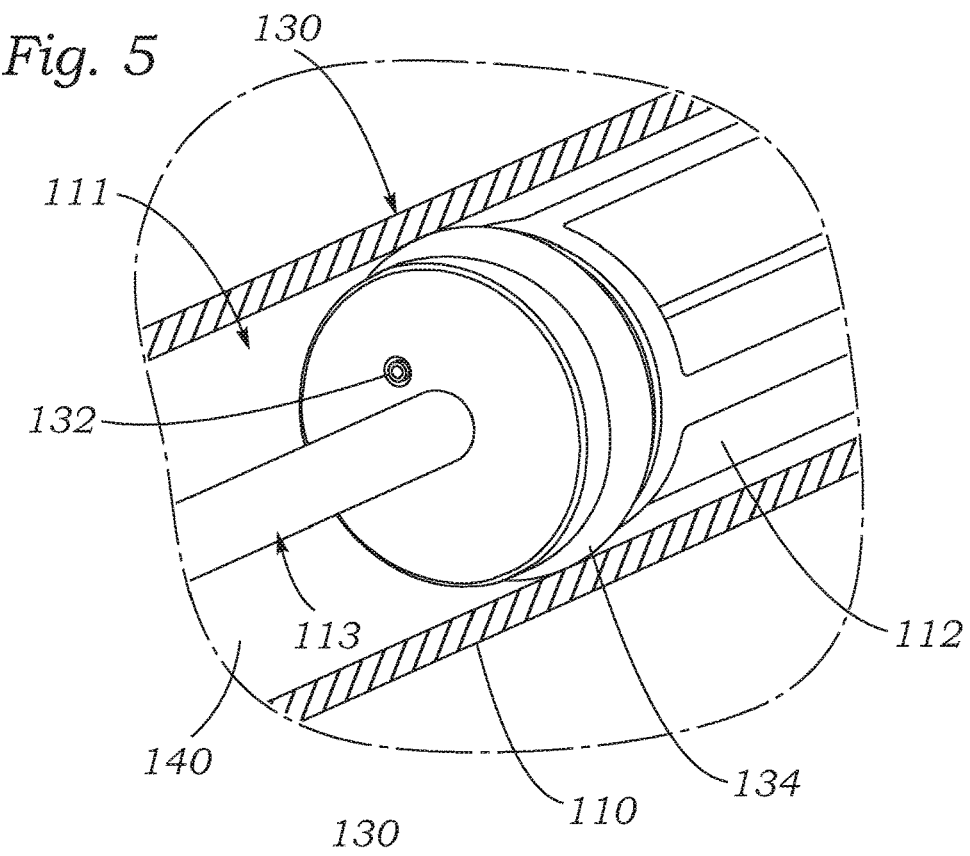
FIG. 5 illustrates a partial sectional view of an injector of an IOL insertion device according to an embodiment of this invention.

Referring to FIG. 5, in an exemplary embodiment, a partial sectional view of the body 110 is shown. As shown in FIG. 2, the plunger 112 includes an elongated distal portion 113. At the proximal end of the portion 113 is a sealing element 130. The sealing element 130 includes a small aperture 132 and a rear seal with an O-ring 134. The outer surface of the O-ring 134 engages the inner surface 140 of the chamber 111 of the body 110, so that fluid in the distal end of the chamber 111 can only pass to the proximal end (as separated by the element 130) of the chamber through the aperture 132.

Figure 6:
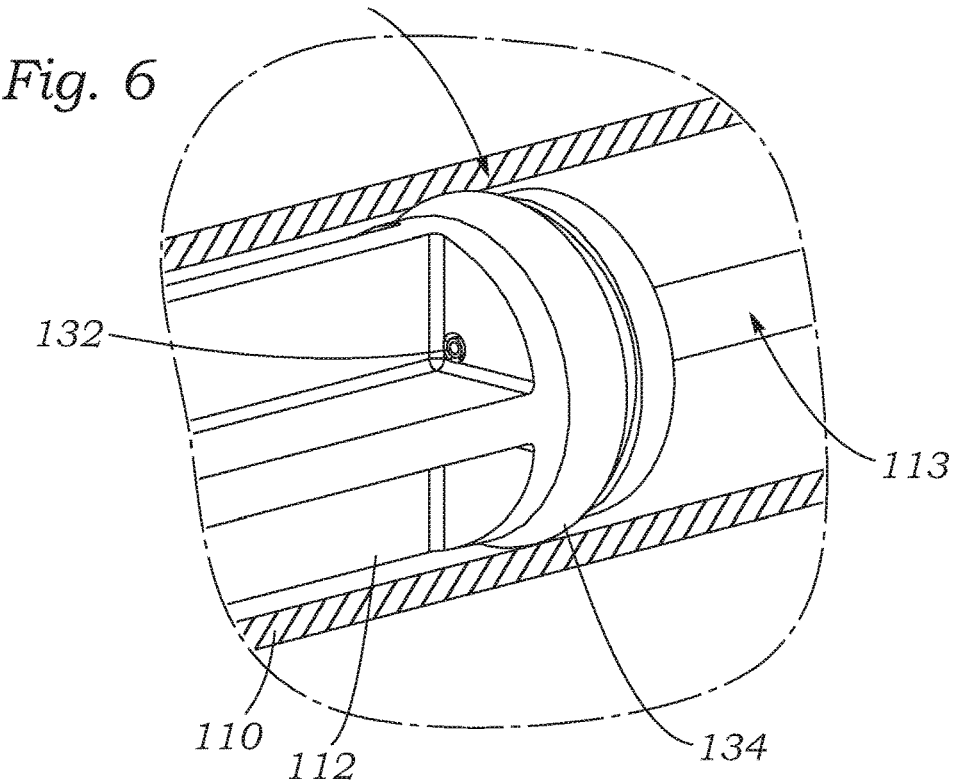
FIG. 6 illustrates another partial sectional view of an injector of an IOL insertion device according to an embodiment of this invention.

FIG. 6, in an exemplary embodiment, shows another partial sectional view of the body 110. In FIG. 6, the proximal view of the element 130 is shown. All features are described as in FIG. 5.

FIG. 7 shows an exemplary embodiment of a perspective view of the insertion device 100. The insertion device 100 includes a cartridge or front modular portion 202, and an injector 102. The injector 102 generally includes a body 110, a distal portion 106, and a plunger 112. While FIG. 7 shows a tubular body 110, the body 110 may also be a polygon or in the shape of a D to control the pushrod orientation. The body 110 includes an aperture 108. The plunger 112 may be of any shape that facilities its movement within the tubular body 110. For example, the plunger 112 may have a hollow enclosed structure as shown in FIG. 7 or a multi-bladed open casing as shown in FIG. 1. It is also envisioned that the plunger 112 may house an O-ring 134. The O-ring 134 may be a part of the plunger 112 or maybe an individual component that can be attached to the plunger 112. The O-ring 134 may have an outer diameter that produces a sliding fit with the inner diameter of the body 110. The distal portion 106 includes the front seal 116. The distal portion 113 of the plunger 112 includes an elongated tip portion 114 (not shown in figure). The elongated tip portion 114 is adapted to pass through a longitudinal, asymmetrical bore 118 (not shown in the figure) in the front seal 116. The elongated tip portion 114 is tapered and is smaller toward the distal end. It is also envisioned that the elongated tip portion 114 may have grooves that facilitate flowing of fluid into the cartridge or front modular portion 202 as the plunger 112 is depressed. The entry of the fluid into the cartridge of front modular portion 202 may serve a hydration or lubrication purpose. The IOL 300 is preloaded into the front modular portion or the cartridge 202. The rear end of the body 110 also includes a vent 109. The vent 109 may be sealed using a plug (not shown in figure) before, during, and/or after the insertion of the IOL 300 into the eye. As will be described herein, the rear vent 109 and the plug allows the end user to drain the fluid from inside the back chamber of the body 110.

Figure 8:
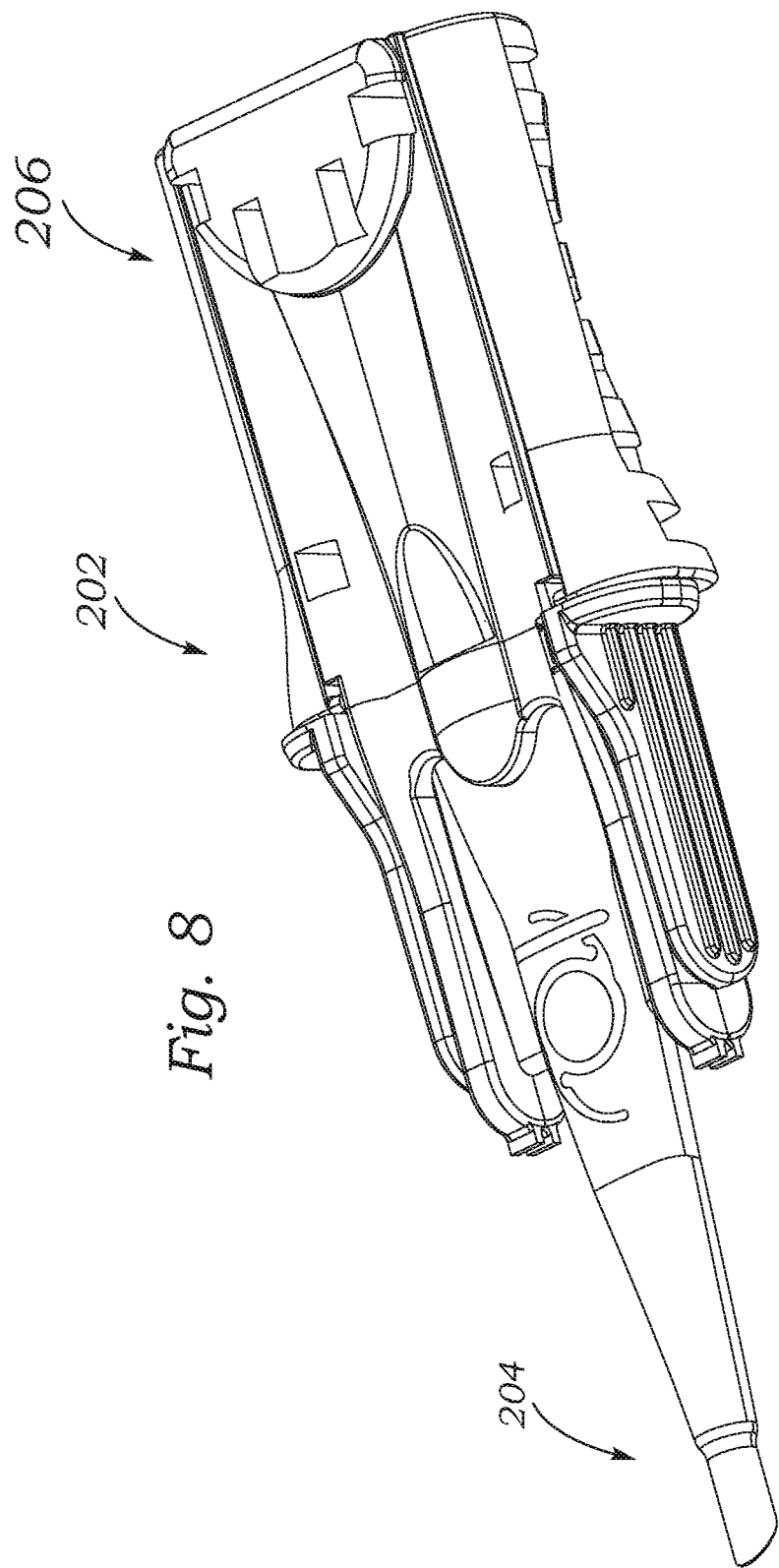
FIG. 8 illustrates a perspective view of a modular portion of an IOL insertion device according to an embodiment of this invention.

Referring to FIG. 8, in an exemplary embodiment, a perspective view of the modular portion 202 is shown. The modular portion 202 includes a distal end 204 and a proximal end 206. An IOL (not shown in the picture) may be preloaded into the modular portion 202. The modular portion 202 may then be coupled at the proximal end 206 with the injector 102, at the distal portion 106 of the injector 102 (as shown in the example in FIG. 1). It is envisioned that the modular portion 202 may be detachable, or it may also be molded so that it is a unitary piece with the distal portion 106 of the injector 102.

FIG. 9, in an exemplary embodiment, shows a perspective view of the bottom of the modular portion 202.

Figure 10:
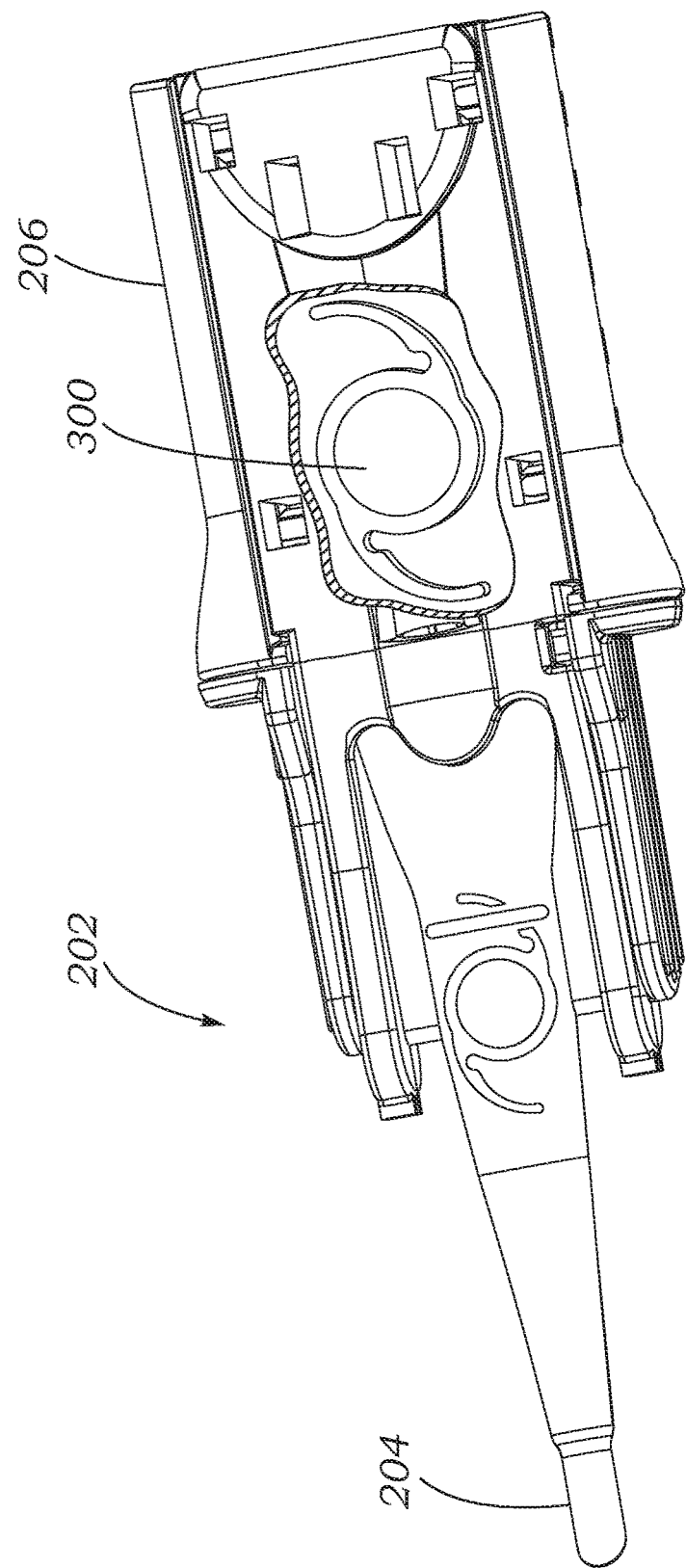
FIG. 10 illustrates a three-dimensional view of a modular portion of an IOL insertion device according to an embodiment of this invention.

Referring to FIG. 10, in an exemplary embodiment, a three-dimensional view of the modular portion 202 shows an IOL 300 when the plunger 112 is in the distally-advanced locked position. The IOL 300 is advanced distally toward the distal end 204 of the modular portion 204, from an initial position at the proximal end 206. In this advanced position, the IOL 300 is ready to be inserted (injected) in the patient's eye.

In some example embodiments, the insertion device 100 operates and functions as follows. An IOL 300 is preloaded into the cartridge or modular portion 202. The proximal end 206 of the modular portion 202 is snapped into (engaged with) the distal portion 106 of the injector 102. A fluid, such as water or a viscoelastic substance or a BSS and the like, is inserted into the chamber 111 of the body 110 through the aperture 108. When the chamber 111 is filled with the fluid (e.g., BSS), the flap 126 in the front seal 116 initially prevents the fluid from entering the modular portion 202 where the IOL 300 is located. While fluid is being inserted into the chamber 111, the plunger 112 is in a proximally retracted position so that the element 130 and O-ring 134 are proximally behind (toward the rear of) the aperture 108. After the chamber 111 is filled, the plunger 112 is pressed, twisted, or twisted and pressed to advance distally along the longitudinal length of the body 110. The fluid passes through the bore 118, by the flap 126, and enters the modular portion 202, thus hydrating and lubricating the cartridge 202 and IOL 300. When the stop 104 rests against the flange 105 (the plunger 112 is stopped), the wider portion of the elongated tip portion 114 fully engages the longitudinal, asymmetrical bore 118 of the front seal 116. In this engaged position, no fluid will pass through the longitudinal, asymmetrical bore 118 from the chamber 111 into the modular portion 202. Also, at this position, the IOL 300 is ready to be loaded (be inserted). Also, as the plunger 112 is further pressed, twisted, or pressed and twisted distally towards the engaged position, the fluid will exit proximally (rearward) through the aperture 132 on the element 130, and into the proximal (rear) end of the chamber 111, which is proximally behind the element 130. The capture of fluid in the proximal end of chamber 111 reduces the tendency of the fluid to spill and/or enter the operating space. Because the aperture 132 is small, as the fluid passes through it, the force needed to depress the plunger 112 is controlled. This force is accommodative or adaptive in that it increases as the user increases force on the plunger 112, thus ensuring a steady release of the IOL 300. The fluid may then exit of the insertion device 100 through the aperture 108 on the body 110. This also ensures dampening of acceleration that occurs as the IOL 300 is being released to prevent popping.

In some example embodiments, the insertion device 100 operates and functions as follows. An IOL 300 is preloaded into the cartridge or modular portion 202. The proximal end 206 of the modular portion 202 is snapped into (engaged with) the distal portion 106 of the injector 102. A fluid, such as water or a viscoelastic substance or a BSS and the like, is inserted into the chamber 111 of the body 110 through the aperture 108. While fluid is being inserted into the chamber 111, the plunger 112 is in a proximally retracted position so that the element 130 and the O-ring 134 is proximally behind (toward the rear of) the aperture 108. When the chamber 111 is filled with the fluid (e.g., BSS), the flap 126 in the front seal 116 initially prevents the fluid from entering the modular portion 202 where the IOL 300 is located. After the chamber 111 is filled, the plunger 112 is pressed, twisted, or twisted and pressed to advance distally along the longitudinal length of the body 110. As the plunger 112 is advanced distally, the elongated tip portion 114 of the plunger 112 breaks open the flap 126. The fluid passes through the bore 118, by the flap 126, and enters the modular portion 202, thus hydrating and lubricating the cartridge 202 and IOL 300. When the stop 104 rests against the flange 105 (the plunger 112 is stopped), the wider portion of the elongated tip portion 114 fully engages the longitudinal, asymmetrical bore 118 of the front seal 116. In this engaged position, no fluid will pass through the longitudinal, asymmetrical bore 118 from the chamber 111 into the modular portion 202. Also, at this position, the IOL 300 is ready to be loaded (be inserted). Also, as the plunger 112 is advanced, the O-ring 134 will position itself under the aperture 108, thereby sealing the aperture 108 from inside the body 110. The O-ring 134 maybe attached to the sealing element 130 or to any other part of the plunger 112. The O-ring 134 may seal the aperture 108 at the engaged position or may seal the aperture 108 before the plunger 112 reaches the engaged position. Additionally, as the plunger 112 is pressed, twisted, or pressed and twisted distally towards the engaged position, the fluid will exit proximally (rearward) through the aperture 132 on the element 130, and into the proximal (rear) end of the chamber 111, which is proximally behind the element 130. Consequently, the fluid in the rear end of the chamber 111, will be sealed within the rear end of the chamber 111 because of the sealing element 130 and the O-ring 134. Because the aperture 132 is small, as the fluid passes through it, the force needed to depress the plunger 112 is controlled. This force is accommodative or adaptive in that it increases as the user increases force on the plunger 112, thus ensuring a steady release of the IOL 300. This also ensures dampening of acceleration that occurs as the IOL 300 is being released to prevent popping.

In some example embodiments, the insertion device 100 operates and functions as follows. An IOL 300 is preloaded into the cartridge or modular portion 202. The proximal end 206 of the modular portion 202 is snapped into (engaged with) the distal portion 106 of the injector 102. A fluid, such as water or a viscoelastic substance or a BSS and the like, is inserted into the chamber 111 of the body 110 through the aperture 108. Prior to the insertion of the fluid into the aperture 108, a plug may be used to close the aperture 108. The end user can unplug the aperture 108 and fill the fluid in the chamber 111 and close the aperture 108 using the plug, subsequently. The plug may be inserted during the manufacture process after preloading the fluid into the body 110 to avoid spillage during packing and storage. While fluid is being inserted into the chamber 111, the plunger 112 is in a proximally retracted position so that the element 130 and the O-ring 134 is proximally behind (toward the rear of) the aperture 108. When the chamber 111 is filled with the fluid (e.g., BSS), the flap 126 in the front seal 116 initially prevents the fluid from entering the modular portion 202 where the IOL 300 is. After the chamber 111 is filled, the plunger 112 is pressed, twisted, or twisted and pressed to advance distally along the longitudinal length of the body 110. As the plunger 112 is advanced distally, the elongated tip portion 114 of the plunger 112 breaks open the flap 126. The fluid passes through the bore 118, by the flap 126, and enters the modular portion 202, thus hydrating and lubricating the cartridge 202 and IOL 300. When the stop 104 rests against the flange 105 (the plunger 112 is stopped), the wider portion of the elongated tip portion 114 fully engages the longitudinal, asymmetrical bore 118 of the front seal 116. In this engaged position, no fluid will pass through the longitudinal, asymmetrical bore 118 from the chamber 111 into the modular portion 202. Also at this position, the IOL 300 is ready to be loaded (be inserted). Additionally, as the plunger 112 is pressed, twisted, or pressed and twisted distally towards the engaged position, the fluid will exit proximally (rearward) through the aperture 132 on the element 130, and into the proximal (rear) end of the chamber 111, which is proximally behind the element 130. Due to the aperture 108 being sealed by the plug, the fluid in the rear end of the chamber 111, will be sealed within the rear end of the chamber 111 because of the sealing element 130 and the plug. Because the aperture 132 is small, as the fluid passes through it, the force needed to depress the plunger 112 is controlled. This force is accommodative or adaptive in that it increases as the user increases force on the plunger 112, thus ensuring a steady release of the IOL 300. This also ensures dampening of acceleration that occurs as the IOL 300 is being released to prevent popping. It is also envisioned that in addition to the plug, the O-ring 134 can also be used to seal the aperture 108 as explained above. The rear end of the chamber 111 may also have a vent 109 that can be closed using the same plug that was used to close aperture 108 once the aperture 108 is sealed by the O-ring 134 or using a different plug. The end user may unplug the vent 109 in the rear end of the chamber 111 to drain the fluid from the rear end of the chamber 111.

In some example embodiments, the insertion device 100 operates and functions as explained above, except that the plunger 112 may be an enclosed hollow casing such that the fluid from the front end of the chamber 111 passes through the aperture 132 on the sealing element 130 into the plunger 112. In such an embodiment, the O-ring 134 may or may not be used to seal the aperture 108. The plug may still be used to close the aperture 108 before and after filling the chamber 111 with the fluid. Additionally, the plunger 112 may have a vent 109 in its rear end that can be sealed by the same plug used to close the aperture 108 or another plug. The end user may unplug the vent 109 in the rear end of the plunger 112 to drain the fluid from inside the plunger 112.

In some example embodiments, the insertion device 100 operates and functions as explained above, except that the O-ring 134 is not firmly attached to the sealing element 130 or the plunger 112. Rather the O-ring 134 can slide freely along the plunger 112 and advance distally as the plunger 112 advances distally. The aperture 108 may have a locking mechanism, such as grooves or a protrusion, near it to lock the O-ring 134 under the aperture 108. Therefore, when the plunger 112 advances distally, the O-ring 134 advances distally and reaches the aperture 108. When the O-ring 134 reaches the aperture 108, the O-ring 134 engages with the locking mechanism near the aperture 108. In the engaged position, the O-ring 134 does not advance distally even when the plunger 112 advances distally. When the O-ring 134 is in the engaged position, it sits firmly under the aperture 108, thereby, sealing the aperture 108.

The previous description of the disclosure is provided to enable any person skilled in the art to make or use the disclosure. Various modifications to the disclosure will be apparent to those skilled in the art, and the generic principles defined herein may be applied to other variations without departing from the scope of the disclosure. Thus, the disclosure is not intended to be limited to the examples and designs described herein, but is to be accorded the widest scope consistent with the principles and novel features disclosed herein.

What is claimed is:

1. A system for injecting an intraocular lens in a controlled manner, comprising:
   an injector having a hollow body extending longitudinally to a distal portion leading to a distal opening;
   a cartridge configured to hold the intraocular lens, the cartridge being coupled to the distal portion of the injector;
   a plunger adapted to slide longitudinally within the hollow body, the plunger having a distal elongated tip and a proximal end that extends out of the hollow body and is configured to be manually depressed, wherein a sealing element separates the proximal end from the elongated tip and is sized to contact and seal against an inner wall of the hollow body and define proximal and distal chambers of the hollow body, the elongated tip having a narrow distal section that tapers to a wider proximal section and a length such that the elongated tip extends out of the distal opening in the hollow body into the cartridge and urges the intraocular lens out of the cartridge when the plunger is fully depressed;
   a front seal located at a distal end of the hollow body having a bore, the elongated tip of the plunger arranged to pass through the bore with the narrow distal section being sized smaller and the wider proximal section being sized larger than an inner diameter of the bore, wherein the bore has a flap at a distal end thereof that extends inward and contacts the narrow distal section of the elongated tip to initially prevent fluid from passing through the seal prior to manually depressing the plunger, and wherein the distal chamber of the hollow body is filled with a lubricating fluid around the elongated tip, the fluid being pressurized upon manually depressing the plunger and the flap is configured to open from the pressurized fluid and permit fluid to flow through the front seal bore around the narrow distal section of the elongated tip and distal opening into the cartridge so as to hydrate and lubricate the cartridge and intraocular lens, and wherein continued distal movement of the elongated tip eventually moves the wider proximal section into the bore which seals the bore and prevents further passage of lubricating fluid through the bore.

2. The system of claim 1, wherein the narrow distal section of the elongated tip has grooves that facilitate flow of lubricating fluid into the cartridge.

3. The system of claim 1, wherein the cartridge is detachable from the injector.

4. The system of claim 1, wherein the cartridge is a unitary piece with the injector.

5. The system of claim 1, wherein the plunger includes a stop toward the proximal end and the hollow body has an outwardly-extending flange which the stop is configured to contact to prevent further distal movement of the plunger.

6. The system of claim 1, wherein the sealing element has a small aperture through which lubricating fluid passes when the plunger advances distally and after the wider proximal section extends into and seals the bore such that a force needed to depress the plunger is controlled by the flow rate of lubricating fluid through the aperture.

7. The system of claim 1, wherein the proximal end of the hollow body has a vent.

8. The system of claim 1, wherein the sealing element includes an O-ring that seals against the inner wall of the hollow body.

9. The system of claim 1, wherein the hollow body has an aperture through a side wall for filling the hollow body with lubricating fluid.

10. The system of claim 9, wherein the sealing element includes an O-ring that seals against the inner wall of the hollow body and seals the aperture in a distal-most position of the plunger.

11. A system for injecting, an intraocular lens in a controlled manner, comprising:
   an injector having a hollow body extending longitudinally to a distal portion leading to a distal opening;
   a cartridge configured to hold the intraocular lens, the cartridge being coupled to the distal portion of the injector;
   a plunger adapted to slide longitudinally within the hollow body, the plunger having a distal elongated tip and a proximal end that extends out of the hollow body and is configured to be manually depressed, wherein a sealing element separates the proximal end from the elongated tip and is sized to contact and seal against an inner wall of the hollow body, the sealing element having a small aperture which connects proximal and distal chambers of the hollow body, the elongated tip having a narrow distal section that tapers to a wider proximal section and a length such that the elongated tip extends out of the distal opening in the hollow body into the cartridge and urges the intraocular lens out of the cartridge when the plunger is fully depressed;
   a front seal located at a distal end of the hollow body having a bore, the elongated tip of the plunger arranged to pass through the bore with the narrow distal section being sized smaller and the wider proximal section being sized larger than an inner diameter of the bore, wherein the distal chamber of the hollow body is filled with a lubricating fluid around the elongated tip, the fluid being pressurized upon manually depressing the plunger to cause lubricating fluid to flow around the narrow distal section of the elongated tip through the front seal bore and distal opening into the cartridge so as to hydrate and lubricate the cartridge and intraocular lens, and wherein continued distal movement of the elongated tip eventually moves the wider proximal section into the bore which seals the bore and prevents further passage of lubricating fluid through the bore, and a force needed to depress the plunger is subsequently controlled by the flow rate of lubricating fluid through the aperture in the sealing element.

12. The system of claim 11, wherein the narrow distal section of the elongated tip has grooves that facilitate flow of lubricating fluid into the cartridge.

13. The system of claim 11, wherein the cartridge is detachable from the injector.

14. The system of claim 11, wherein the cartridge is a unitary piece with the injector.

15. The system of claim 11, wherein the plunger includes a stop toward the proximal end and the hollow body has an outwardly-extending flange which the stop is configured to contact to prevent further distal movement of the plunger.

16. The system of claim 11, wherein the proximal end of the hollow body has a vent.

17. The system of claim 11, wherein the sealing element includes an O-ring that seals against the inner wall of the hollow body.

18. The system of claim 11, wherein the hollow body has an aperture through a side wall for filling the hollow body with lubricating fluid.

19. The system of claim 18, wherein the sealing element includes an O-ring that seals against the inner wall of the hollow body and seals the aperture in a distal-most position of the plunger.

* * * * *